(12) United States Patent
Kura

(10) Patent No.: US 8,753,261 B2
(45) Date of Patent: Jun. 17, 2014

(54) ENDOSCOPE APPARATUS

(75) Inventor: Yasuhito Kura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 248 days.

(21) Appl. No.: 12/953,681

(22) Filed: Nov. 24, 2010

(65) Prior Publication Data

US 2011/0071355 A1 Mar. 24, 2011

Related U.S. Application Data

(63) Continuation of application No. 11/894,876, filed on Aug. 22, 2007, now abandoned, which is a continuation of application No. PCT/JP2006/302380, filed on Feb. 10, 2006.

(30) Foreign Application Priority Data

Feb. 23, 2005 (JP) ................. 2005-047851

(51) Int. Cl.
*A61B 1/00* (2006.01)
*A61B 1/04* (2006.01)
*A61B 18/00* (2006.01)

(52) U.S. Cl.
CPC ........... *A61B 1/00156* (2013.01); *A61B 1/0016* (2013.01); *A61B 2018/00196* (2013.01); *A61B 2018/00202* (2013.01); *A61B 2018/00208* (2013.01); *A61B 1/00133* (2013.01)
USPC ........... 600/106; 600/114; 600/117; 600/137

(58) Field of Classification Search
CPC ................. A61B 1/00156; A61B 2018/00196; A61B 2018/00202; A61B 2018/00208; A61B 1/00133; A61B 1/0016
USPC ........................................................ 600/114
See application file for complete search history.

(56) References Cited

U.S. PATENT DOCUMENTS

| | | | |
|---|---|---|---|
| 4,327,878 A | | 5/1982 | Fauchier et al. |
| 4,374,525 A | * | 2/1983 | Baba ............................ 600/463 |
| 4,982,725 A | * | 1/1991 | Hibino et al. ................. 600/117 |
| 4,998,282 A | | 3/1991 | Shishido et al. |
| 5,060,632 A | * | 10/1991 | Hibino et al. ................. 600/109 |
| 5,124,789 A | * | 6/1992 | Hiyama et al. .................. 348/74 |
| 5,308,354 A | * | 5/1994 | Zacca et al. .................... 606/159 |
| 5,314,438 A | * | 5/1994 | Shturman ...................... 606/159 |
| 5,430,665 A | | 7/1995 | Jin et al. |

(Continued)

FOREIGN PATENT DOCUMENTS

| | | |
|---|---|---|
| JP | 55-42657 | 3/1980 |
| JP | 10-113396 | 5/1998 |
| JP | 2000-107123 | 4/2000 |
| JP | 2001-170000 | 6/2001 |

*Primary Examiner* — Alireza Nia
(74) *Attorney, Agent, or Firm* — Scully, Scott, Murphy & Presser, P.C.

(57) ABSTRACT

An endoscope apparatus comprises an insertion portion having an observation optical system attached onto the distal end portion thereof and having flexibility, a thrust generating portion for generating a thrust by rotation, formed beyond a predetermined length on an outer-peripheral surface of the insertion portion in a longitudinal-axis direction, a rotation device for rotating the thrust generating portion around the longitudinal axis, and a control portion for controlling a rotational speed of the thrust generating portion according to an insertion length of the thrust generating portion inserted in a subject.

25 Claims, 9 Drawing Sheets

(56) References Cited

U.S. PATENT DOCUMENTS

| | | | |
|---|---|---|---|
| 5,502,606 A * | 3/1996 | Mori et al. | 360/291.7 |
| 5,728,044 A | 3/1998 | Shan | |
| 5,810,858 A | 9/1998 | Berman et al. | |
| 5,840,024 A * | 11/1998 | Taniguchi et al. | 600/424 |
| 5,957,833 A * | 9/1999 | Shan | 600/117 |
| 5,989,230 A | 11/1999 | Frassica | |
| 6,004,271 A * | 12/1999 | Moore | 600/445 |
| 6,494,890 B1 | 12/2002 | Shturman et al. | |
| 7,048,717 B1 * | 5/2006 | Frassica | 604/165.04 |
| 7,511,733 B2 * | 3/2009 | Takizawa et al. | 348/68 |
| 7,637,864 B2 * | 12/2009 | Yokoi et al. | 600/114 |
| 2003/0222638 A1 | 12/2003 | Twerdochlib | |
| 2004/0186368 A1 | 9/2004 | Ramzipoor et al. | |
| 2004/0243148 A1 | 12/2004 | Wasielewski | |
| 2006/0270901 A1 | 11/2006 | Bern et al. | |
| 2007/0265547 A1 | 11/2007 | Trabada et al. | |
| 2009/0302147 A1 | 12/2009 | Emoto | |

* cited by examiner

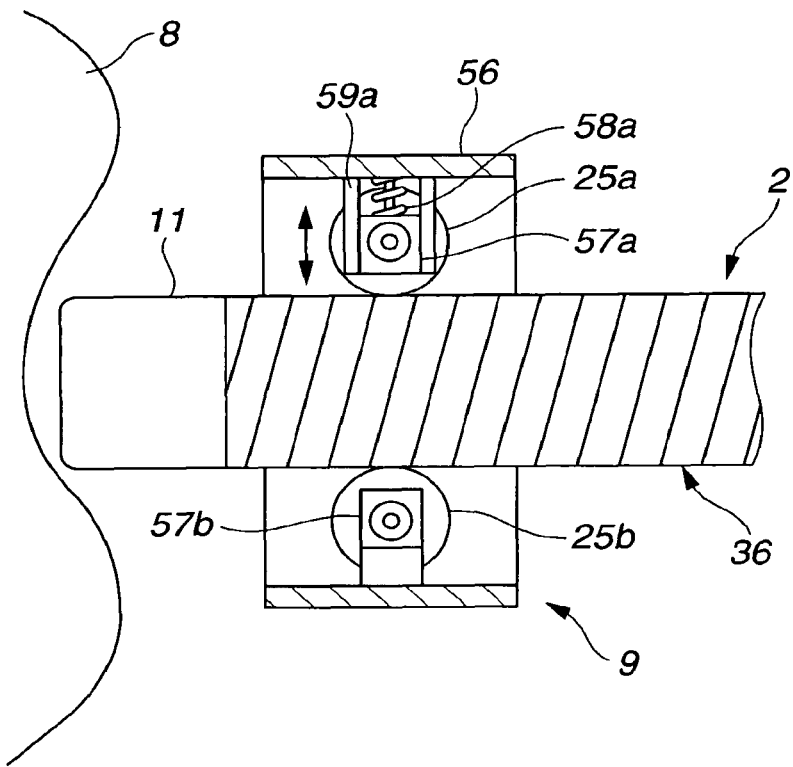
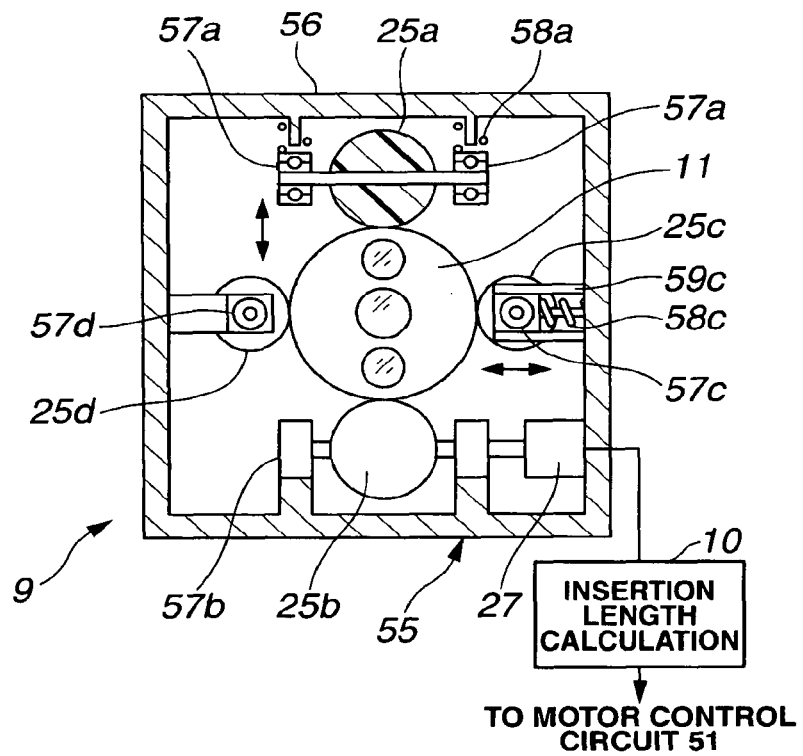

ENDOSCOPE APPARATUS

CROSS REFERENCE TO RELATED APPLICATION

This application is a continuation application of U.S. patent application Ser. No. 11/894,876 filed on Aug. 22, 2007, which is a continuation application of PCT/JP2006/302380 filed on Feb. 10, 2006 and claims benefit of Japanese Application No. 2005-047851 filed in Japan on Feb. 23, 2005, the entire contents of which is incorporated herein by this reference.

BACKGROUND OF THE INVENTION

1. Field of the Invention

The present invention relates to an endoscope apparatus suited to smoothly insert a flexible insertion portion into a bending body cavity.

2. Description of the Related Art

There has been widely available an endoscope which can observe organs in a body cavity and perform various types of treatments and procedures by inserting a flexible insertion portion into the body cavity such as a large intestine.

Considerable skill is required to smoothly insert an insertion portion into a body cavity complexly bending like a large intestine. An inexperienced operator may lose track of an insertion direction while inserting an insertion portion to a deep region, which may cause the operator to confront insertion difficulty. Accordingly, various types of proposals have been made to improve ease of inserting an insertion portion.

For example, Japanese Patent Laid-Open Publication No. 10-113396 describes a medical appliance propelling device which can guide a medical appliance up to a deep region of an organism canal easily and less invasively. The medical appliance propelling device has a rotary member rotatably disposed immediately before the distal end of a medical appliance. An outer-peripheral surface of the rotary member is formed with a rib slanting relative to an axial direction.

Accordingly, rotation of the rotary member permits a rotational force of the rotary member to be transformed into a propelling force by the rib. Then, the propelling force moves the medical appliance connected to the propelling device in a direction of the deep region.

SUMMARY OF THE INVENTION

An endoscope apparatus according to the present invention comprises: an insertion portion having an observation optical system attached onto the distal end thereof having flexibility; a thrust generating portion for generating a thrust by rotation, formed beyond a predetermined length on an outer-peripheral surface of the insertion portion in a longitudinal-axis direction; a rotation device for rotating the thrust generating portion around the longitudinal axis; and a control portion for controlling a rotational speed of the thrust generating portion in accordance with an insertion length of the thrust generating portion inserted into a subject.

BRIEF DESCRIPTION OF THE DRAWINGS

FIG. 4 is a longitudinal sectional view showing an internal configuration of an insertion guide portion;

FIG. 5 is a front view including a sectional view showing an internal configuration of an insertion guide portion;

DETAILED DESCRIPTION OF THE PREFERRED EMBODIMENT(S)

Embodiment of the present invention will now be described in detail with reference to the drawings.

Figure 1:
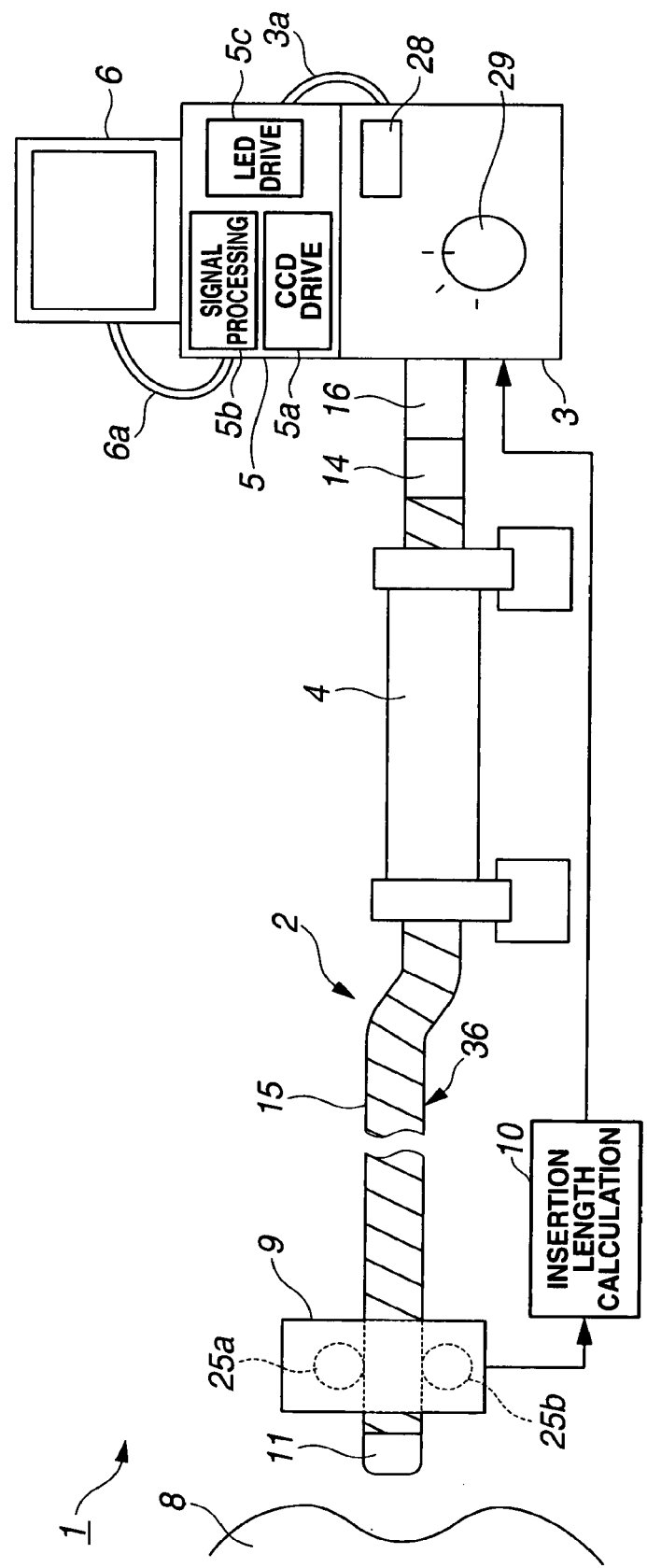
FIG. 1 is a view showing an overall configuration of an endoscope apparatus in a first embodiment according to the present invention.
Figure 2:
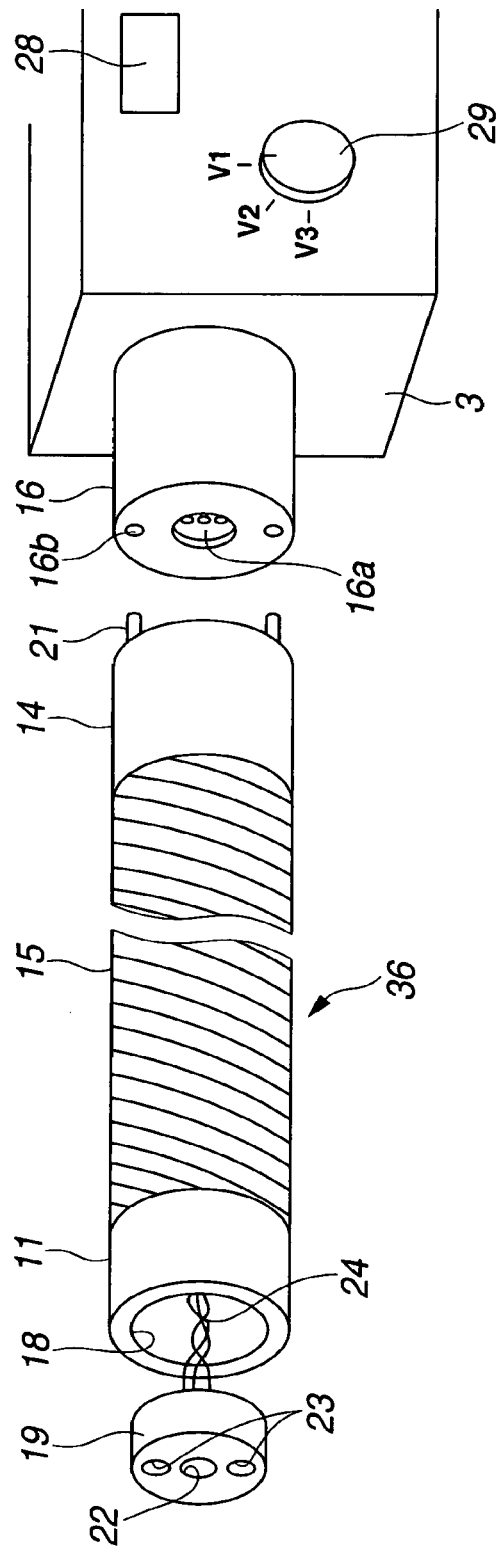
FIG. 2 is a perspective view showing a configuration of a connection portion between an endoscope insertion portion and an endoscope rotation device.
Figure 3:
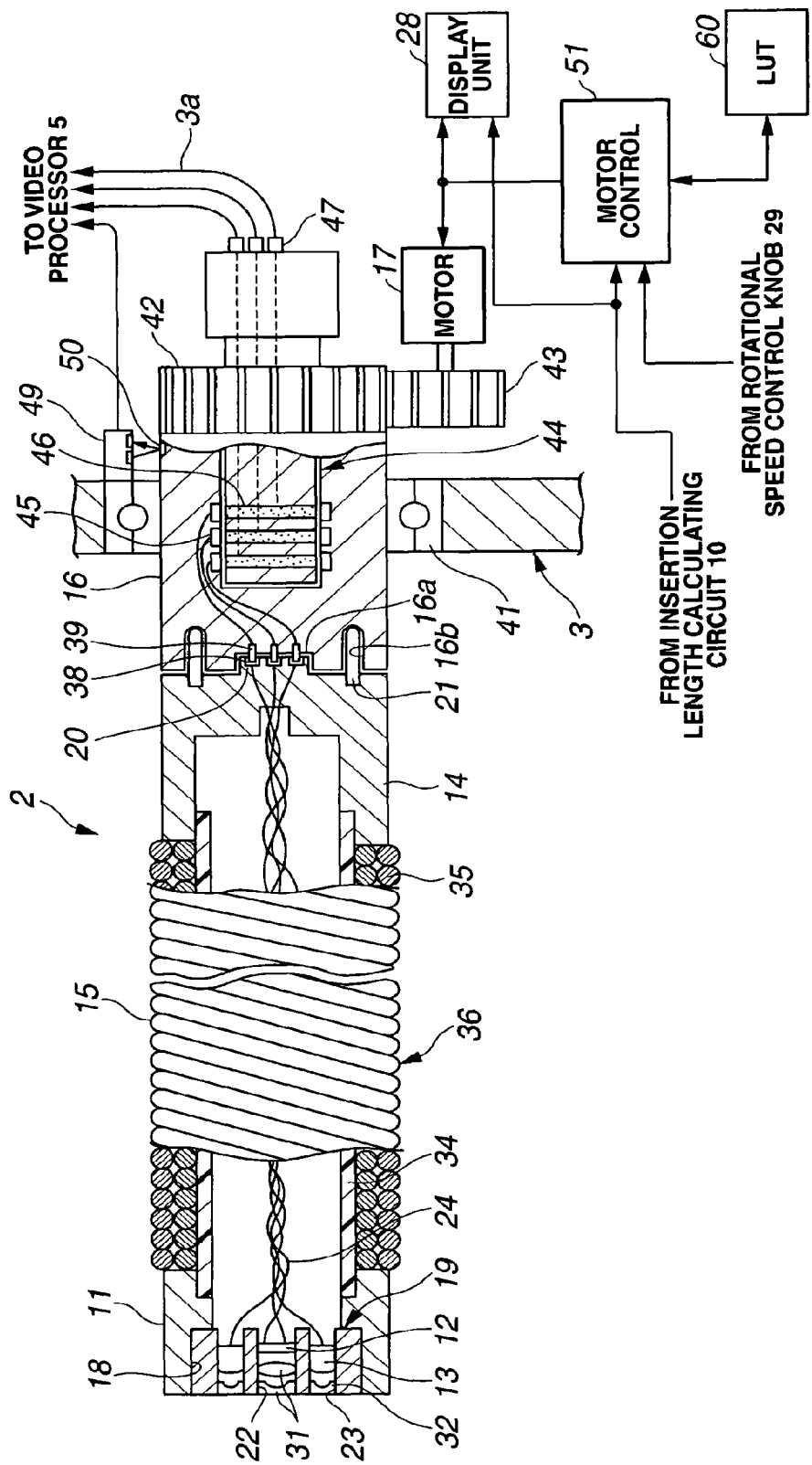
FIG. 3 is a sectional view showing an internal configuration of the endoscope insertion portion and that of the rotation device.

Referring to FIGS. 1 to 5, a first embodiment of the present invention will be described below. FIG. 1 shows an overall configuration of an endoscope apparatus in a first embodiment according to the present invention, FIG. 2 shows a configuration of a connection portion between an endoscope insertion portion and an endoscope rotation device, FIG. 3 shows an internal configuration of the endoscope insertion portion and that of the rotation device 3, and FIGS. 4 and 5 show a configuration of an insertion guide portion, respectively.

As shown in FIG. 1, an endoscope apparatus 1 in a first embodiment according to the present invention comprises an endoscope insertion portion 2, a rotation device 3, a protective tube 4, a video processor 5, a monitor 6, an insertion guide portion 9 and an insertion length calculation circuit 10.

The endoscope insertion portion 2 is slender and flexible. The rotation device 3 rotates the endoscope insertion portion 2. The protective tube 4 rotatably retains the endoscope insertion portion 2. The video processor 5 performs signal processing. The monitor 6 displays an image captured by the endoscope insertion portion 2. The insertion guide portion 9 is inserted into a body cavity of a patient 8 as a subject. The insertion length calculating circuit 10 calculates, for example, an insertion length of the endoscope insertion portion 2. The insertion length calculating circuit 10 comprises a control portion for controlling rotational speeds of the endoscope insertion portion 2 according to insertion lengths of the endoscope insertion portion 2.

The endoscope insertion portion 2 is slender and has a rigid distal end portion 11 on the distal end thereof. The distal end portion 11 includes a charge coupled device (CCD) 12 (refer to FIG. 3) as an image pickup device described later and a light emitting diode (abbreviated as "LED") 13 (refer to FIG. 3) as illumination means. The endoscope insertion portion 2 is inserted into the protective tube 4 for preventing touching a floor in an operating room. The rear end (proximal end) of the endoscope insertion portion 2 is formed with a connector 14 and the connector 14 is detachably connected to an insertion portion retainer 16 provided to the rotation device 3.

An outer-peripheral surface between the distal end portion 11 in the endoscope insertion portion 2 and the connector 14 is formed with a propelling tube (guide tube) 15 as a thrust generating portion for generating a thrust force by rotation. Rotating a motor 17 (refer to FIG. 3) provided inside the rotation device 3 permits rotation of the propelling tube 15 provided on an outer-peripheral surface of the endoscope insertion portion 2. This enables a propelling force to be produced high enough to propel the endoscope insertion portion 2 into a body cavity.

That is to say, in the present embodiment, the propelling tube 15 (configured of a spiral shape portion 36 described later) has a length close to the overall length of the slender endoscope insertion portion 2 to form a thrust force generating portion. This provides a thrust force high enough to propel the endoscope insertion portion 2 even if the propelling tube 15 is rotated at a relatively low speed.

In the present embodiment, the rotation portion rotated by the rotation device 3 serves as the endoscope insertion portion 2 with which the propelling tube 15 is integrally formed (in an endoscope insertion portion 90 shown in FIG. 8 described later, the rotation portion is configured such that only a propelling tube portion 102 on the outer-peripheral side rotates).

The CCD12 and LED13 in the endoscope insertion portion 2 are connected to a slip ring 44 (refer to FIG. 3) in the rotation device 3 by a signal cable 24 inserted through the endoscope insertion portion 2. Furthermore, the CCD12 and LED13 are connected to the video processor 5 through a signal cable 3a from the rotation device 3.

The video processor 5 includes a CCD drive circuit 5a, a signal processing circuit 5b and a LED drive circuit 5c. The CCD drive circuit 5a supplies a CCD drive signal. The signal processing circuit 5b performs signal processing for an image pickup signal output from the CCD12 to produce an image signal. The LED drive circuit 5c supplies a drive signal for light-emitting of an LED13.

Image signals produced by the signal processing circuit 5b are output to the monitor 6 through the cable 6a. This permits an image captured by the CCD12 to be displayed on the screen of the monitor 6.

In inserting the endoscope insertion portion 2 described later into a body cavity such as a large intestine, the video processor 5 controls so that only still pictures are displayed on the screen of the monitor 6 at predetermined rotational angles when the endoscope insertion portion 2 is rotated.

In the present embodiment, in inserting the endoscope insertion portion 2 into the body cavity of a patient 8, the insertion guide portion 9 is disposed near the patient 8. The endoscope insertion portion 2 is inserted into the insertion guide portion 9 which enables the insertion portion 2 to be inserted into the patient. The endoscope insertion portion 2 can then be inserted into the body cavity of the patient 8, for example, the large intestine.

The insertion guide portion 9, as described in FIGS. 4 and 5 later, includes spheres 25a, 25b rotating in contact with an outer-peripheral surface of the endoscope insertion portion 2. For example, the sphere 25b rotating in an insertion-axis direction of the endoscope insertion portion 2 is a traveling-amount detection mechanism, which is equipped with a sensor for detecting the rotational amount of the sphere 25b (specifically, for example, a rotary encoder 27 in FIG. 5). The sensor comprises a traveling-amount detection mechanism and output signals from the sensor are inputted into the insertion length calculating circuit 10. The insertion length calculating circuit 10 calculates output signals from the sensor and determines an insertion length of the endoscope insertion portion 2 into a body cavity.

As shown in FIG. 2, the distal end portion 11 of the endoscope insertion portion 2 is formed with a cylindrical camera unit (or image pickup unit) storage portion 18. The camera unit storage portion 18 stores and fixes a camera unit (image pickup unit) 19 including an observation optical system and an illumination optical system.

A rear end surface of the connector 14 provided at the rear end of the endoscope insertion portion 2 is formed with a projection portion 20 (refer to FIG. 3) in the center thereof. The periphery of the projection portion 20 is formed with, for example, two projecting pins 21.

The projection portion 20 in the connector 14 is fitted into a recessed portion 16a formed in the center of the distal end surface of the insertion portion retainer 16 projecting from the rotation device 3 in a substantially columnar shape. The pin 21 is fitted into a pin hole 16b formed in the periphery of the recessed portion 16a. This permits the connector 14 to be detachably connected to the insertion portion retainer 16 of the rotation device 3.

In the present embodiment, the outside diameter of the connector 14 is almost the same as, for example, that of the endoscope insertion portion 2.

The camera unit 19 mounted on the camera unit storage portion 18 at the distal end portion 11 is formed with an observation window 22 substantially in the center of the distal end surface. At a plurality of positions around the observation window 22, two points in the present embodiment, respectively, an illumination window 23 is formed. A plurality of signal cables 24 are extended from the proximal end side of the camera unit 19 and inserted into the endoscope insertion portion 2. The signal cables 24 are connected with the video processor 5 through the rotation device 3.

In the present embodiment, the rotational speed of the motor 17 in the rotation device 3 can be controlled so as to be automatically set to an appropriate value, based on information of an insertion length detected by the insertion length calculating circuit 10.

Moreover, the rotation device 3 is mounted with, for example, a display unit 28 for displaying rotational speeds with the motor 17 and insertion lengths.

The rotation device 3 is mounted with a rotational speed control knob 29 as a setter for manually setting, for example, rotational speeds with the motor 17. A user such as an operator can manually control rotational speeds with the motor 17 by operating the rotational speed control knob 29, based on a rotational speed or an insertion length to be displayed.

Referring next to FIG. 3, a configuration of the endoscope insertion portion 2 and the rotation device 3 will be described in detail below.

FIG. 3 is a longitudinal sectional view of FIG. 2 and shows an internal configuration. Moreover, a part of the propelling tube 15 is shown with a side view.

As shown in FIG. 3, the observation window 22 provided in the center of the camera unit 19 fixed on the distal end portion 11 is attached with an objective optical system (or observation optical system) 31 forming optical images of an object and CCD12. The CCD12 is disposed at an image-forming position of the objective optical system 31.

The two illumination windows 23 adjacent to the observation window 22 is attached with the LED13 and the illumination optical system 32. The LED13 produces illumination light. The illumination optical system 32 expands the light emitted by the LED 13 and outputs the light from the illumination window 23.

Further, from the proximal end of the camera unit 19, are extended a signal cable connected to the CCD12 and transmitting CCD driving and image pickup signals and a signal cable 24 connected to the LED13 and transmitting drive signals for driving LED light emitting.

On the rear end of the distal end portion 11, there is fixed one distal end of an insertion portion covering tube 34 which has flexibility and constitutes the insertion portion body, hereinafter referred to as a "covering tube". The rear end of the covering tube 34 is connected to the rigid connector 14. The outer-peripheral surface of the covering tube 34 is installed with the propelling tube 15.

The propelling tube 15 is disposed at an outer-periphery portion of the covering tube 34 between the distal end portion 11 of the endoscope insertion portion 2 and the connector 14 at the rear end. The propelling tube 15, made of, for example, stainless is formed so as to have predetermined flexibility by winding a metallic strand 35 of a predetermined diameter into two layers in a spiral manner. The propelling tube 15 may be formed by winding the metallic strand 35 into more layers (e.g. four layers) in a spiral manner.

For the metallic strand 35 wound in a spiral manner, a degree of tightness between the metallic strands 35 and spiral angles are variously set. The outer surface of the propelling tube 15 is formed with the spiral shape portion (spiral propelling portion) 36 in a spiral shape having uneven portions formed by a surface of the metallic strand 35.

The spiral shape portion 36 may be formed with spiral uneven portions on an outer-peripheral surface of a member constituting the endoscope insertion portion 2, in addition to forming a spiral shape with uneven portions by winding the metallic strand 35 in a spiral shape.

The spiral shape portion 36 is formed so as to be sufficiently long over almost the overall length of the endoscope insertion portion 2. That is, the spiral forming portion is formed so as to be longer than a predetermined length. Accordingly, even if the propelling tube 15 is rotated at a relatively low speed, the endoscope insertion portion 2 can be propelled by a sufficient propelling force. That is, in the present embodiment, the thrust generating portion for generating thrust by rotating the endoscope insertion portion 2 around the longitudinal axis thereof is configured of the spiral shape portion 36.

In the present embodiment, the propelling tube 15 is provided on an outer-peripheral surface on a little more backward side than the distal end portion 11. Accordingly, the propelling tube 15 will not hinder a view by an observation optical system provided at the distal end portion 11. This permits a user to perform propelling operations while observing.

Preferably, the metallic strand 35 is formed so as to be wound in a left-handed spiral shape facing toward the proximal end from the distal end. In other words, it is preferable that the metallic strand 35 be spirally wound in the same direction as a left handed thread groove. In such a configuration, in inserting the endoscope insertion portion into a body cavity, especially a large intestine, the insertion portion retainer 16 of the rotation device 3 is rotated counter-clockwise around the longitudinal axis of the endoscope insertion portion 2. Then, tightness to a intestinal wall in the large intestinal becomes higher, thus improving the insertability of the endoscope insertion portion 2 into the large intestinal.

A substantially columnar projection portion 20 is formed substantially in the center of a rear end surface of the connector 14 and, around the projection portion 20, for example, two pins 21 are formed.

The projection portion 20 is fitted into the recessed portion 16a in the insertion portion retainer 16. On the other hand, the two pins 21 are fitted into the pin holes 16b. This permits the connector 14 to be connected to the insertion portion retainer 16. Accordingly, when the insertion portion retainer 16 is rotated, the connector 14 is rotated.

Moreover, an end surface of the projection port 20 is formed with a plurality of contact pin receivers 38. The contact pin receivers 38 are connected with a plurality of signal cables 24 respectively. In connecting the connector 14 with the insertion portion retainer 16, the contact pin receivers 38 of the connector 14 come into contact with a plurality of contact pins 39 provided at the recessed portion 16a in the insertion portion retainer 16 each other. This permits the CCD12 and LED13 to be electrically connected with the contact pins 39 of the rotation device 3.

The outer-peripheral surface of the insertion portion retainer 16 is rotatably supported by bearings 41 provided at a casing of the rotation device 3. On the outer-peripheral surface of the proximal end of the insertion portion retainer 16, a gear 42 is provided. The gear 42 is located on a more backward side than such a position that the gear is rotatably supported by the bearings 41.

The gear 42 engages with a cylindrical gear 43 provided on the distal end of a motor shaft of the motor 17. The motor 17 is rotated around the longitudinal axis in a predetermined direction, for example, counterclockwise facing toward the distal end from the proximal end, by which the endoscope insertion portion 2 rotates.

Moreover, the insertion portion retainer 16 is provided with a slip ring 44. A recessed portion is provided around the central axis to be rotated from the rear end surface side of the insertion portion retainer 16. The recessed portion has a rotor-side contact 45 constituting a slip ring 44 therein. Furthermore, the recessed portion has a cylindrical rotor constituting the slip ring 44 therein. Around the rotor, the rotor-side contact 45 is provided to make an electric connection with a stator-side contact 46. The contact pin 39 and the contact 45 are electrically connected with each other through a signal line.

The rotor-side contact 45 rotating, being connected with the contact pin 39 by the slip ring 44 and the stator-side contact 46 not to be rotated are maintained in a contact state for electric conductivity. The stator-side contact 46 is connected with the contact 47 at the rear end through a signal line in the slip ring 44. The contact 47 is connected with a signal cable 3a. The signal cable 3a is electrically connected with the video processor 5.

The casing of the rotation device 3 is provided with a sensor for detecting a predetermined rotational angle (rotational position) in the insertion portion retainer 16, for example, a photo reflector 49. The photo reflector 49 irradiates light onto an outer-peripheral surface of the insertion portion retainer 16 and receives the reflected light. The photo reflector 49 is disposed, for example, near such a position that the bearing 41 is provided.

In this case, a light reflection portion 50 with high reflectance is disposed at a predetermined position in an outer-peripheral surface of the insertion portion retainer 16. The light reflectance of other portions is set so as to be lower than that of a light reflection portion 50. Location of the light reflection portion 50 corresponds to a predetermined direction, for example, upward direction of the CCD 12.

Accordingly, in a case where the endoscope insertion portion 2 connected to the insertion portion retainer 16 is rotatingly driven by the motor 17, the photo reflector 49 for detecting reflected light from light reflection portion 50 detects the timing when the CCD12 reaches a predetermined angle. A timing signal detected by the predetermined angle is inputted into the signal processing circuit 5b of the video processor 5.

The signal processing circuit 5b alternately overwrites images captured by the CCD12 on two frame memories inside the signal processing circuit 5b in a cycle where the insertion portion retainer 16 is once rotated. When a timing signal of reaching a predetermined angle is inputted from the photo reflector 49, a memory control circuit (not shown) for controlling read/write of the frame memory prohibits read/write of one frame memory performing overwriting by the input timing.

Images written in the frame memory immediately before the timing signal are maintained until the next timing.

At this time, an image read from the one frame memory is displayed on the monitor 6 as a still image. In this case, the other frame memory is overwritten until the next timing. Then, writing is prohibited at the next timing in the same way and an image is read as a still image from the frame memory.

In this way, a still image captured at a timing of a predetermined angle is continuously displayed on the monitor 6 with the endoscope insertion portion 2 being rotated.

The number of predetermined positions in an outer-peripheral surface of the insertion portion retainer 16 is taken as one for simplification herein, but a plurality of positions may be used.

In that case, after respective predetermined positions are detected, captured images are rotated according to the rotational angles. At that time, always focusing on a direction of one position as a datum, images detected at a plurality of positions are displayed. Increasing the number of predetermined positions in this way enables the monitor 6 to display still images in a state nearer to moving pictures.

For the motor 17 for rotatingly driving the insertion portion retainer 16, rotational speeds are controlled by a motor control circuit 51. The motor control circuit 51 constitutes the control portion.

In the present embodiment, the motor control circuit 51 permits the rotational speed of the motor 17 to be manually controlled by operating the rotational speed control knob 29, for example, provided on a front panel in the rotation device 3. The rotational speed control knob 29 changes a parameter of a motor control system, for example, by changing a value of variable resistance.

In other words, in inserting the endoscope insertion portion 2 into a body cavity, differences may occur in appropriate insertion speeds among operators. Accordingly, rotational speeds can be adjusted within an allowable rotational speed range by an operator's operating the rotational speed control knob 29. FIG. 2 shows that adjustment can be made between V1 and V3.

In the present embodiment, there is provided the insertion guide portion 9 configured as shown in FIGS. 4 and 5. The insertion guide portion 9 includes a mechanism for detecting the rotational amount of a rotation member rotating in contact with the propelling tube 15 forming an outer-peripheral surface of the endoscope insertion portion 2.

More specifically, the rotational amount of the sphere 25b as a rotation member per unit time is detected. In other words, rotational speeds are detected and the detected rotational speeds are inputted into the insertion length calculating circuit 10 for calculation. This permits calculation of an insertion length of the endoscope insertion portion 2 or the spiral shape portion 36 and automatic adjustment of the rotational speed of the motor 17 through a motor control circuit 51 based on information of the calculated insertion length.

In the present embodiment, the spiral shape portion 36 is formed from around the front end of the endoscope insertion portion 2 to around the rear end of the endoscope insertion portion 2. Accordingly, in detecting an insertion length inserted in a body cavity, detection of an insertion length of the endoscope insertion portion 2 may be used in place of detection of an insertion length of the spiral shape portion 36.

In other words, the insertion length portion of the spiral shape portion 36 actually inserted in the body cavity has a function of a propelling force generating portion which generates a propelling force by rotating. However, the portion may be considered as generating a propelling force by rotating the insertion length portion of the endoscope insertion portion 2 inserted in the body cavity.

In a case where the spiral shape portion 36 is formed only at a part of an outer-peripheral surface on the distal end side of the endoscope insertion portion 2, it may be better to detect an insertion length of the spiral shape portion 36, which depends upon an insertion length to be inserted into a body cavity.

The motor control circuit 51 outputs a motor drive signal for rotatingly driving the motor 17 and the motor drive signal is inputted into the display unit 28. This permits a rotational speed of the motor 17 to be displayed on the display unit 28. An output signal from the insertion length calculating circuit 10 is inputted into the motor control circuit 51 and then into the display unit 28. Accordingly, an insertion length as well is displayed on the display unit 28.

Referring next to FIGS. 4 and 5, a configuration of an insertion length detection portion 55 provided to the insertion guide portion 9 will be described below. FIG. 4 is a longitudinal sectional view showing an internal configuration of the insertion guide portion 9 and FIG. 5 is a front view including a lateral sectional view showing an internal configuration of the insertion guide portion 9.

On the top and bottom sides of around the center of a frame body 56 comprising the insertion guide portion 9, a pair of spheres 25a, 25b for rotatably retaining the endoscope insertion portion 2 to be inserted so as to sandwich the endoscope insertion portion 2 between the spheres from the vertical direction. Each of the spheres 25j (j=a, b) has a rotating shaft extended in such a direction as to be orthogonal to the insertion axis of the endoscope insertion portion 2. The each rotating shaft is rotatably supported by bearings 57j provided on both sides of the each sphere 25j.

In this case, a stator of the one bearing, specifically, the bearing 57b on the lower side in FIG. 4 is fixed on an inner wall of the frame body 56. The other bearing 57a is retained movably in the vertical direction so as to be forced downward by the elastic force of a spring 58a.

Even if uneven portions exist in the spiral shape portion 36 on an outer-peripheral surface of the endoscope insertion portion 2, the spheres 25a, 25b come into contact with the outer-peripheral surface. The spheres 25a, 25b, when the endoscope insertion portion 2 travels in the direction of the insertion axis, is rotated by the traveling amount. The stator side of the movable bearing 57a is disposed between the guide members 59*a* fixed on the frame body 56, which regulates the rotation. A bearing 58*c* described later is disposed between the guide members 59*c* likewise to regulate the rotation.

As shown in FIG. 5, the rotating axis of the one sphere 25*b* is connected to a rotary encoder 27. The rotary encoder 27 detects the rotational amount of the sphere 25*b* or rotational speed and outputs the detected signal to the insertion length calculating circuit 10.

The insertion length calculating circuit 10 calculates an insertion length of the endoscope insertion portion 2 inserted in the body cavity of a patient 8 by calculating detected signals from the rotary encoder 27 and outputs the calculated length into the motor control circuit 51 of the rotation device 3.

As shown in FIG. 3, the motor control circuit 51 is connected with a lookup table (abbreviated as LUT) 60. The LUT60 previously stores data to set an appropriate rotational speed according to an insertion length. The LUT60 is a rotational speed information storage portion and constitutes the control portion.

The motor control circuit 51 reads data of an appropriate rotational speed from LUT60 according to the calculated insertion length and automatically sets rotational speed to the appropriate one. The LUT60 comprises, for example, an electrically rewritable nonvolatile memory and can update data to more appropriate one, for example, through the motor control circuit 51.

Moreover, LUT60 stores data which is set to a fixed speed when an insertion length is smaller than a predetermined value, for example, like the initial state in inserting, and which decelerates rotational speed as an insertion length is larger (longer). The data can be updated when more preferable data is available.

As shown in FIG. 5, the two spheres 25*c*, 25*d* are disposed likewise in the horizontal direction of an area where the endoscope insertion portion 2 is inserted, and are rotatably retained in contact with an outer-peripheral surface of the endoscope insertion portion 2.

In this case, the rotating axes of both the spheres 25*c*, 25*d* are extended in a direction parallel to the insertion axis, each of which is rotatably retained by the bearings 57*c*, 57*d*. The one bearing 57*d* is fixed on an inner wall of the frame body 56 and the other bearing 57*c* is forced on the central side by an elastic force of the spring 58*c*. Thus, the spheres 25*c*, 25*d* are rotatably retained around the insertion axis in contact with an outer-peripheral surface of the endoscope insertion portion 2 from the horizontal direction.

The operation of the present embodiment in such a configuration will be described below.

As shown in FIG. 1, the connector 14 on the proximal end side of the endoscope insertion portion 2 is connected to the insertion portion retainer 16 of the rotation device 3 via the inside of the protective tube 4.

In conducting colon examination, the distal end portion of the endoscope insertion portion 2 is inserted from the anus as an insert opening into the body cavity of a patient 8, via the insertion guide portion 9. At this time, by turning on of a source of power (not shown), the motor 17 is rotated.

Then, rotating the motor 17 permits the endoscope insertion portion 2 to rotate. On an outer-peripheral surface of the endoscope insertion portion 2, the spiral shape portion 36 is provided, and rotation of the spiral shape portion 36 produces a propelling force. Accordingly, an operator can smoothly insert the endoscope insertion portion 2 into a body cavity at low boost pressure as compared to a case where no propelling force is produced. Images captured by the CCD12 during insertion, though still images, can be observed without narrowing field of view. Accordingly, an operator can insert the endoscope insertion portion 2 while observing images.

When the endoscope insertion portion 2 is inserted into a body cavity, an insertion length into the body cavity changes. As the insertion length of the endoscope insertion portion 2 is larger, a propelling force is apt to become larger. In the present embodiment, however, the insertion length detection portion 55 provided to the insertion guide portion 9 detects a traveling speed of the endoscope insertion portion 2 in the insertion-axis direction, that is, an insertion speed.

The insertion length calculating circuit 10 calculates an insertion length based on insertion speed and outputs the calculated information into the motor control circuit 51 in the rotation device 3. The motor control circuit 51 reads corresponding information of appropriate rotational speeds from the LUT 60 based on the calculated information and, even if the insertion length is changed, always performs automatic control to appropriate rotational speed.

Accordingly, the present embodiment enables an operator, in inserting the endoscope insertion portion 2 into the deep portion in a body cavity, to automatically conduct smooth insertion at an appropriate rotational speed according to an insertion length without need of rotational speed control. Accordingly, endoscopic examination can be made smoothly in a short time for an area to be inspected.

Figure 6:
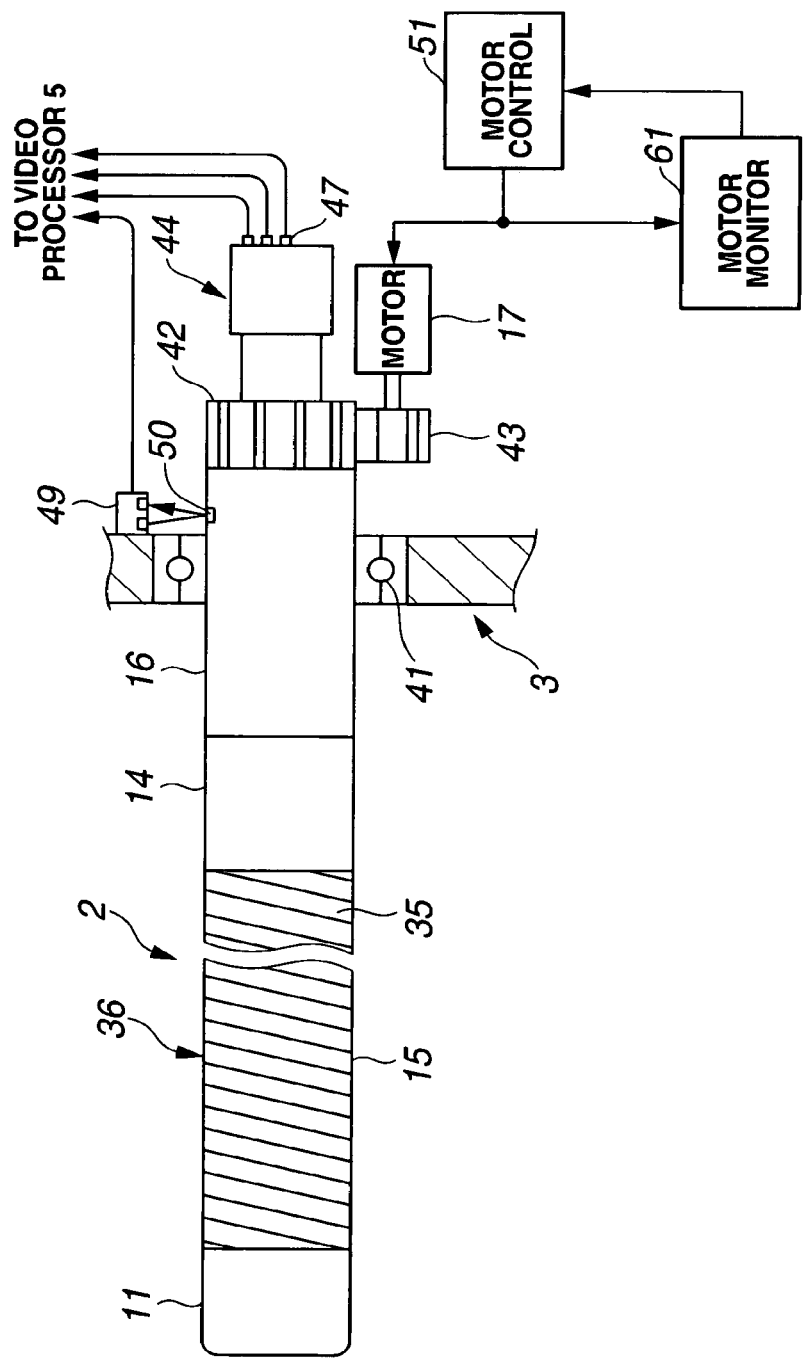
FIG. 6 is a view showing a configuration around a connection portion between an endoscope insertion portion and an endoscope rotation device in a second embodiment according to the present invention.

Referring next to FIG. 6, a second embodiment of the present invention will be described below. FIG. 6 shows a configuration around a connection portion between an endoscope insertion portion and an endoscope rotation device in a second embodiment.

The first embodiment is configured so that the insertion length detection portion 55 provided to the insertion guide portion 9 detects an insertion speed of the endoscope insertion portion 2 or the spiral shape portion 36 (or propelling tube 15) provided at an outer-peripheral surface thereof into a body cavity, and so that the insertion length calculating circuit 10 calculates an insertion length into the body cavity and controls a rotational speed of the motor 17. On the other hand, the present embodiment is configured so that a motor monitor circuit 61 provided as a control portion controls a rotational speed of the motor 17.

In the present embodiment, the motor monitor circuit 61 monitors a motor drive signal supplied to the motor 17 from the motor control circuit 51. According to the monitoring result, the motor monitor circuit 61 outputs a rotation control signal into the motor control circuit 51 to control a rotational speed of the motor 17.

Specifically, the motor monitor circuit 61 monitors voltage value and current values of motor drive signals to be applied to the motor 17. Furthermore, the motor monitor circuit 61 determines, for example, whether the motor 17 rotates in an almost no-load state or in a state in which the endoscope insertion portion 2 is inserted into a body cavity and a current value exceeds a preset value higher than the current value at no load.

When such a state as to be inserted into a body cavity is determined, the current values are totalized to measure a cumulative amount of rotational speeds of the motor 17. According to the cumulative amount of rotational speeds, an insertion length of the endoscope insertion portion 2 (or the spiral shape portion 36) into a body cavity is calculated (estimated) and the calculated insertion length is output into the motor control circuit 51 to control rotational speeds of the motor 17. The motor control circuit 51 controls the rotational speeds of the motor 17 according to the calculated insertion length, for example, information from the LUT 60 (omitted in FIG. 6) as described in the first embodiment.

In the present embodiment, a maximum load level corresponding to the maximum load is set to the motor 17 with a motor drive current value or the like. When the motor monitor circuit 61 monitors a motor drive signal and determines the monitored motor drive signal is above the maximum load level, the motor monitor circuit 61 transmits a signal to the motor control circuit 51. The motor control circuit 51 controls the motor 17 so as to stop the rotation.

That is, the motor control circuit 51 calculates an insertion length by totalizing current values in such a predetermined range in which motor drive signals range from no load to a reasonable load or in some other way and sets a rotational speed of the motor 17 to an appropriate value based on the calculated insertion length value.

The present embodiment provides estimation of an insertion length of the spiral shape portion 36 or the endoscope insertion portion 2 into a body cavity with a simple configuration. The estimated insertion length can facilitate smooth insertion work of the endoscope insertion portion 2 into the body cavity by use of rotational movement. Furthermore, the present embodiment can prevent a load from being imposed on the motor 17 beyond the allowable value, thus preventing the service life from being impaired.

Figure 7:
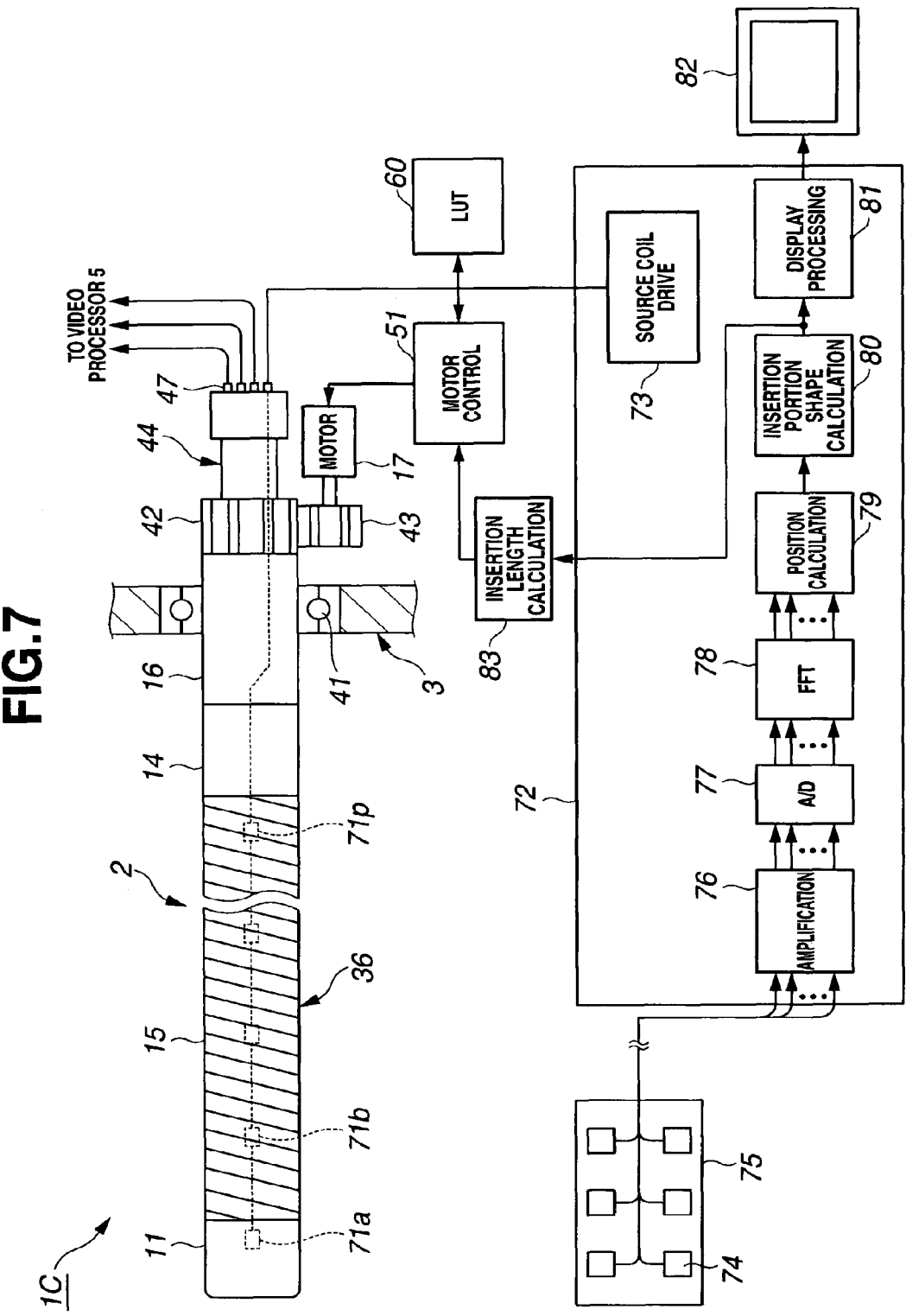
FIG. 7 is a view showing a configuration of a peripheral portion of a circuit for calculating an insertion length in a third embodiment according to the present invention.

Referring next to FIG. 7, a third embodiment of the present invention will be described below. FIG. 7 shows a configuration of a peripheral portion of an insertion length calculating circuit for an endoscope insertion portion in an endoscope apparatus according to a third embodiment.

In an endoscope apparatus 1C, the endoscope insertion portion 2 includes source coils 71a, 71b, ..., 71p as magnetic field generating elements generating magnetic fields arranged at predetermined intervals in the insertion-axis direction to calculate an insertion portion shape. The respective source coils 71k (k=a, b, ..., p) are connected to a source coil drive portion 73 in an insertion shape detector 72 through contacts 47 of the slip ring 44.

From the source coil drive portion 73, AC drive signals of, for example, around 10 kHz are sequentially applied to the respective source coils 71k or simultaneously at different frequencies. Then, the respective source coils 71k generate magnetic fields therearound.

Around a patient into which the endoscope insertion portion 2 is inserted, there is arranged a sense coil unit 75 as a magnetic-field detecting element. The sense coil unit 75 includes a plurality of sense coils 74 to detect magnetic fields generated by the source coil 71k.

Signals detected by the respective sense coils 74 are amplified by an amplifier 76 in the insertion shape detector 72, converted into digital signals by an A/D converter 77 and inputted into a fast Fourier transformation portion 78 (abbreviated as "FFT" in FIG. 7).

After the signals are transformed into frequency components at a high speed by the fast Fourier transformation portion 78, signal components of the same frequency as drive signals of the respective source coils 71k are separated and extracted. The separated and extracted signal components are inputted into a position calculation portion 79, so that the positions of the respective source coils 71k are calculated.

The calculated positional data is transmitted to an insertion portion shape calculating portion 80. The insertion portion shape calculating portion 80 calculates an insertion portion shape of the endoscope insertion portion 2 by conducting interpolation between positional information of the respective source coils 71k or in a similar means.

The calculated insertion portion shape, after being further subjected to image display processing by a display processing circuit 81, is output to a monitor 82 for insertion portion shape display. This permits the insertion portion shape to be displayed on a screen of the monitor 82.

Output signals of the insertion portion shape calculating portion 80 are input into an insertion length calculating portion 83. The insertion length calculating portion 83 calculates an insertion length of the endoscope insertion portion 2 or the spiral shape portion 36 inserted on the inner body cavity side than an insertion opening where the source coil 71a positioned in the distal end portion 11 is inserted in the body of a patient, for example, the anus in the case of a large intestine and outputs the calculated insertion length into the motor control circuit 51.

The motor control circuit 51 reads out the data of a corresponding rotational speed from the LUT 60 based on the data of an insertion length calculated in the same way as for the first embodiment and controls the rotational speed of the motor 17 so as to obtain the rotational speed.

The present embodiment can automatically set the rotational speed to an appropriate one according to the insertion length of the endoscope insertion portion 2 inserted into the body cavity or the spiral shape portion 36 provided on the outer-peripheral surface in the same way as for the first embodiment, and provides easy and smooth insertion of the endoscope insertion portion 2 into the body cavity.

The aforementioned description is made on such a configuration that the propelling tube 15 having the spiral shape portion 36 is integrally formed on the outer-peripheral surface of the endoscope insertion portion 2. However, the present invention is not limited to this. For example, there may be proposed such a configuration that a propelling tube portion is rotatably provided on an outer-peripheral surface of the endoscope insertion portion 2, by which only the propelling tube portion side rotatably provided is rotated and the endoscope insertion portion body side inside thereof is inhibited from rotating.

Figure 8:
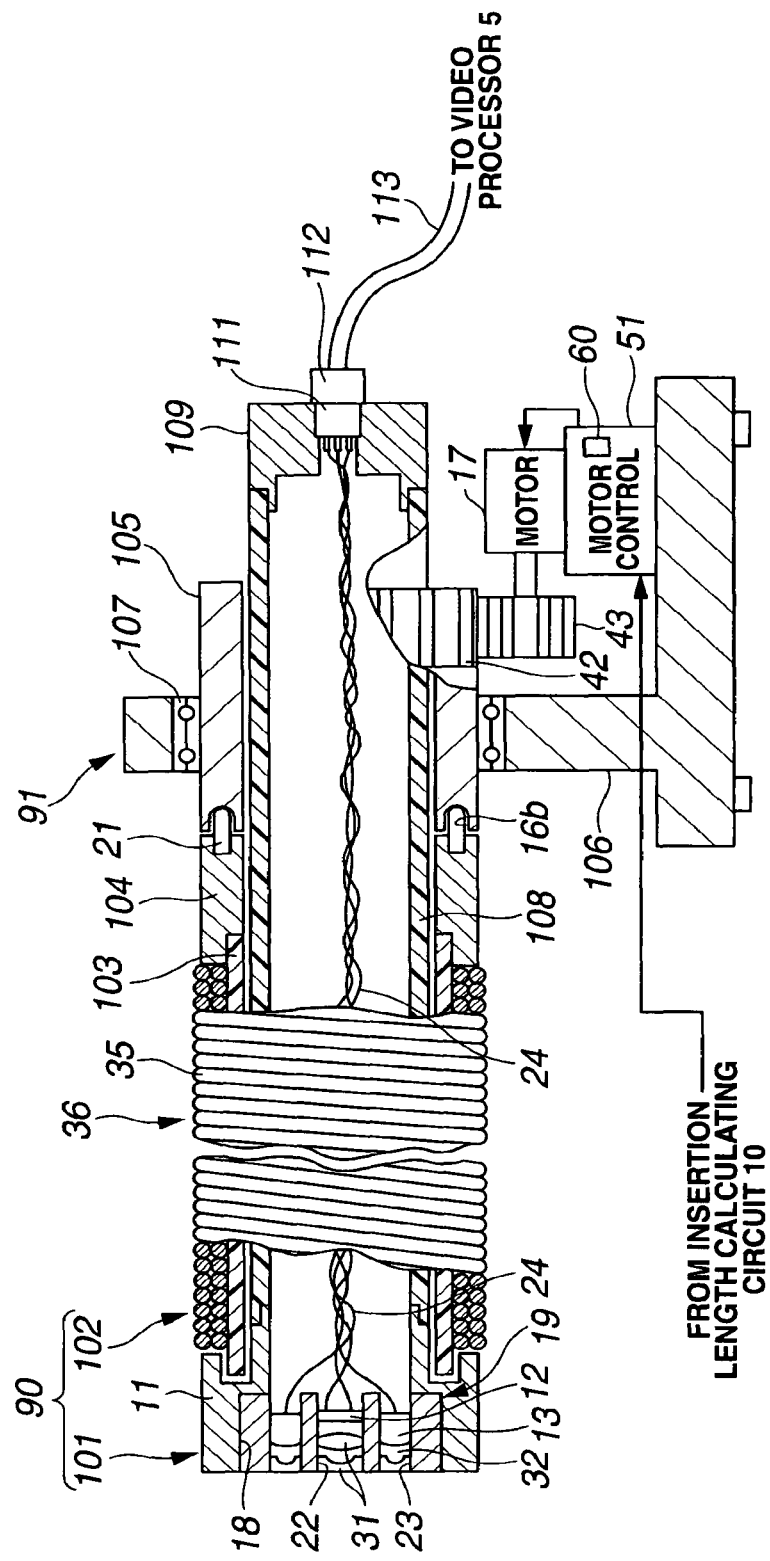
FIG. 8 is a configurational view showing a main portion of an endoscope insertion portion and an endoscope rotation device in a variation example according to the present invention.

FIG. 8 shows a main portion of an endoscope apparatus corresponding to, for example, a variation example of the first embodiment. The endoscope insertion portion 90 in FIG. 8 is configured so as to rotate only the propelling tube portion 102 rotatably disposed on the outer-peripheral surface.

The endoscope insertion portion 90 according to the present embodiment mainly comprises an endoscope body 101 and a propelling tube portion 102 rotatably disposed on the outer-peripheral surface.

The propelling tube portion 102 comprises a flexible outer tube 103 and a spiral shape portion 36 formed of metal line 35. The flexible outer tube 103 is rotatably fitted into an annular recessed portion on the distal end portion 11 of the endoscope body 101. The spiral shape portion 36 is formed on an outer-peripheral surface of the flexible outer tube 103. Further, rear ends of the flexible outer tube 103 and the spiral shape portion 36 are integrally connected to a cylindrical connector 104.

On the rear end of the connector 104, the pin 21 is provided. Inserting the pin 21 into a pin hole 16b at the front end of a cylindrical propelling tube portion retainer 105 permits the propelling tube portion 102 to be detachably connected to the propelling tube portion retainer 105.

The propelling tube portion retainer 105 is rotatably retained onto a rotation retainer 106 through bearings 107. Moreover, on the outer-peripheral surface of the rear end of the propelling tube portion retainer 105, a gears 42 is formed. The gear 42 is engaged with a cylindrical gear 43 formed on a rotating shaft of the motor 17.

The propelling tube portion 102 is configured so as to rotatingly drive the motor 17 by motor drive signals from the motor control circuit 51 provided on a base of the rotation retainer 106 constituting the rotation device 91, thus driving rotation thereof.

The endoscope body 101 is formed with a projection for insertion from around the rear end of the distal end portion 11 toward the inner surface side of the propelling tube portion 102. The distal end of the flexible inner tube 108 is connected to the projection constituting the rear end of the distal end portion 11. The rear end of the flexible inner tube 108 is secured on a rigid flexible tube fixing member 109.

The distal end portion 11 is formed with an observation window 22 and an illumination window 23 in the same way as for the first embodiment.

Signal cables 24 connected to the CCD12 and LED13 are inserted into the flexible inner tube 108 and connected to a contact of the proximal end of the electric connector receiver 111 provided on the flexible tube fixing member 109. The electric connector receiver 111 is detachably connected to an electric connector 112 from backward side.

The cable 113 provided with the electric connector 112 is connected with the video processor 5.

The endoscope insertion portion 90 is inserted into the body cavity of a patient 8, for example, through the insertion guide portion 9 according to the first embodiment. An output of the insertion length detector 55 of the insertion guide portion 9 is input into the motor control circuit 51 as insertion length information through the insertion length calculating circuit 10. In the same way as for the first embodiment, a rotational speed of the motor 17 is controlled according to an insertion length. This configuration has LUT60 in the motor control circuit 51.

Rotating the motor 17 in such a configuration permits only the propelling tube portion 102 formed with the spiral shape portion 36 to rotate. By propelling the propelling tube portion 102 into the body cavity, the distal end of the propelling tube portion 102 presses the rear end of the distal end portion 11 and propels the inner endoscope body 101 as well.

Preferably, bearings are disposed so as to be rotatable in the peripheral direction between the distal end of the propelling tube portion 102 and rear end of the distal end portion 11 opposing thereto.

In this variation, an image pickup device does not rotate. Accordingly, outputting an image captured by the CCD12 permits the monitor 6 to always display a moving picture. Others have equivalent advantages to those for the first embodiment.

In the first embodiment, for example, the traveling amount of each of the bearings 57*a* vertically movably disposed in the spheres 25*a*, 25*b* disposed vertically corresponds to the outside diameter of the endoscope insertion portion 2. Accordingly, detecting the traveling amount of the bearing 57*a* can detect the outside diameter of the endoscope insertion portion 2.

Rotational speed using the motor 17 may be automatically set to an appropriate value according to the outside diameter. In this case, by use of LUT or the like storing information of rotational speeds to be set according to outside diameters, rotational speeds may be automatically set to appropriate values according to outside diameters.

In other words, rotational speed may be set to the one suited to an outside diameter of a spiral shape portion rotationally driven in the endoscope insertion portion 2 and the rotational speed may be adjusted to an appropriate value according to an insertion length into a body to be inspected.

The respective embodiments described above show such a configuration that the spiral shape portion 36 as a thrust generating portion is provided over almost the whole length of the endoscope insertion portion 2. However, the thrust generating portion is not limited to such a configuration as to be provided over the whole length of the endoscope insertion portion. There may be proposed such a configuration that the plurality of spiral shape portions 36*a*, 36*b* are provided at some intervals as shown in FIG. 9, or such a configuration that the spiral shape portion 36 is provided on only the distal end side.

Figure 9:
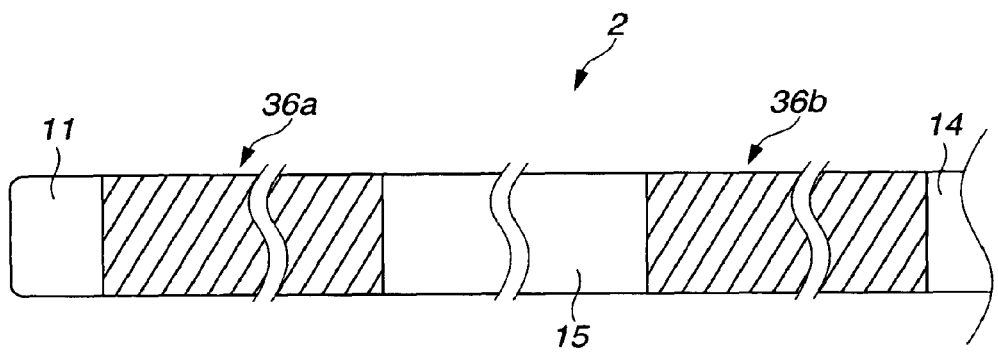
FIG. 9 is a view showing an endoscope insertion portion having a plurality of spiral portions.
Figure 11:
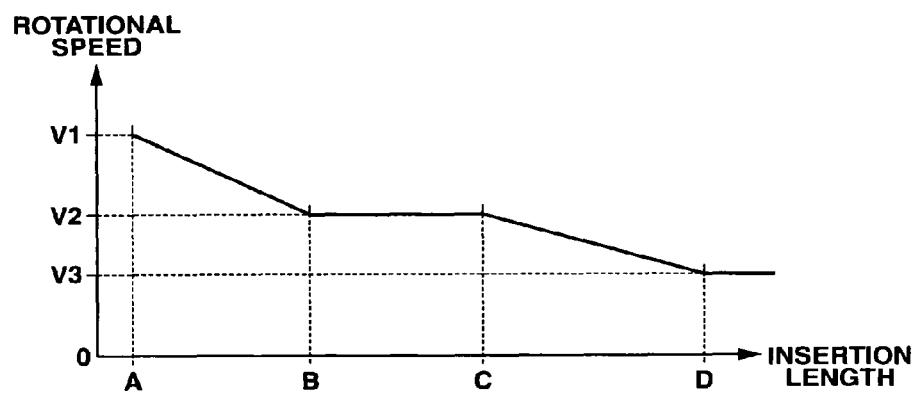
FIG. 11 is a view describing a relationship between insertion lengths of the endoscope insertion portion having the plurality of spiral portions and rotational speeds.

The endoscope insertion portion 2 as shown in FIG. 9 has spiral shape portions 36*a*, 36*b* of predetermined lengths at the distal end portion and midway portion of the propelling tube 15. In the endoscope insertion portion 2 of such a configuration as well, rotational speeds of the motor 17 are automatically adjusted to appropriate ones through the motor control circuit 51 based on information of insertion lengths. At that time, rotational speeds of the propelling tube 15 having the spiral shape portions 36*a*, 36*b* are controlled according to respective insertion lengths of the endoscope insertion portion 2 as shown in FIG. 11. Specifically, for example, when an insertion length of the endoscope insertion portion 2 is a distance A or the distal end of the spiral shape portion 36*a* is inserted into an anus, the rotational speed is V1. As the endoscope insertion portion 2 is further inserted, the rotational speed is continuously decelerated at a predetermined rate from V1. When an insertion length of the endoscope insertion portion 2 is a distance B or the proximal end of the spiral shape portion 36*a* is inserted into the anus, the rotational speed is changed to V2. Until the insertion length is changed from the distance B to a distance C or the distal end of the spiral shape portion 36*b* is inserted into the anus, the rotational speed is maintained at V2. When an insertion length of the endoscope insertion portion 2 is a distance C or the distal end of the spiral shape portion 36*b* is inserted into the anus, the rotational speed is continuously decelerated at a predetermined rate from V2 as the endoscope insertion portion 2 is inserted. When an insertion length of the endoscope insertion portion 2 is a distance D or the proximal end of the spiral shape portion 36*b* is inserted into the anus, the rotational speed is changed to V3. According to this embodiment, similar operation and effect to the abovementioned embodiment can be achieved.

A relationship between lengths of the spiral shape portion 36*a* and the spiral shape portion 36*b* shown in FIG. 9 may be the same or different. An interval between the spiral shape portion 36*a* and the spiral shape portion 36*b* may be set optionally. Furthermore, the plurality of spiral shape portions are not limited to two, but more than two may be used.

Figure 10:
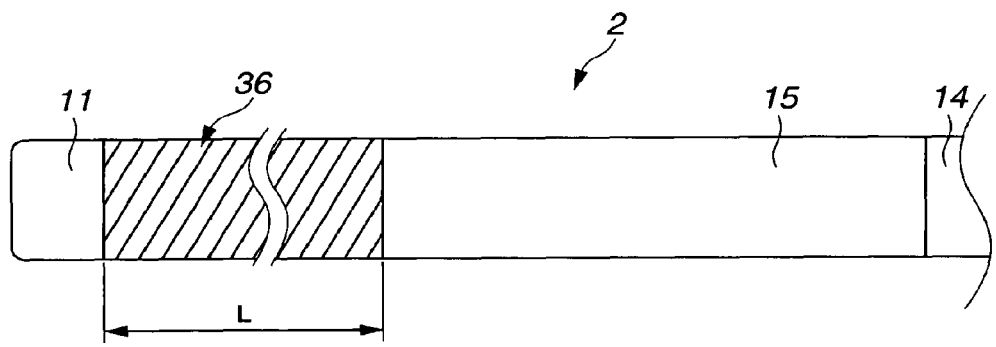
FIG. 10 is a view showing an endoscope insertion portion having a spiral portion set to a predetermined length.
Figure 12:
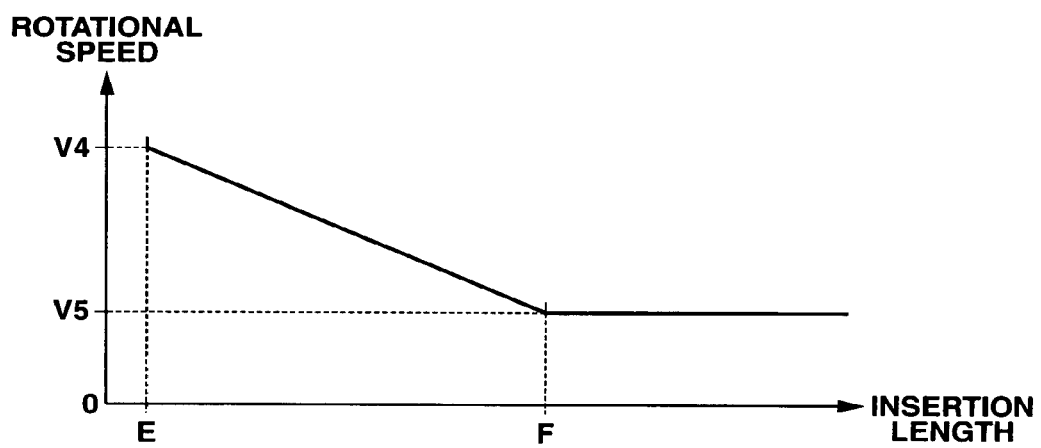
FIG. 12 is a view describing a relationship between changes in insertion lengths of the endoscope insertion portion having the spiral portion set to predetermined lengths and rotational speeds continuously decelerated with the changes.

For the endoscope insertion portion 2 shown in FIG. 10, on the other hand, the spiral shape portion 36 is provided by a predetermined length (L) from the distal end surface as the distal end side of the propelling tube 15. In the endoscope insertion portion 2 of such a configuration as well, rotational speeds of the motor 17 are automatically adjusted to appropriate ones through the motor control circuit 51 based on information of insertion lengths. At that time, rotational speeds of the propelling tube 15 having the spiral shape portion 36 are controlled according to respective insertion lengths of the endoscope insertion portion 2 as shown in FIG. 12. Specifically, for example, when an insertion length of the endoscope insertion portion 2 is a distance E or when the distal end of the spiral shape portion 36 is inserted into the anus, the rotational speed is V4. As the endoscope insertion portion 2 is further inserted, the rotational speed is continuously decelerated at a predetermined rate from V4. When an insertion length of the endoscope insertion portion 2 is a distance F or when the proximal end of the spiral shape portion 36 is inserted into the anus, the rotational speed is changed to V5. While the endoscope insertion portion 2 is being inserted into the body cavity, the rotational speed is maintained at V5. According to this embodiment, similar operation and effect to the abovementioned embodiment can be achieved.

Figure 13:
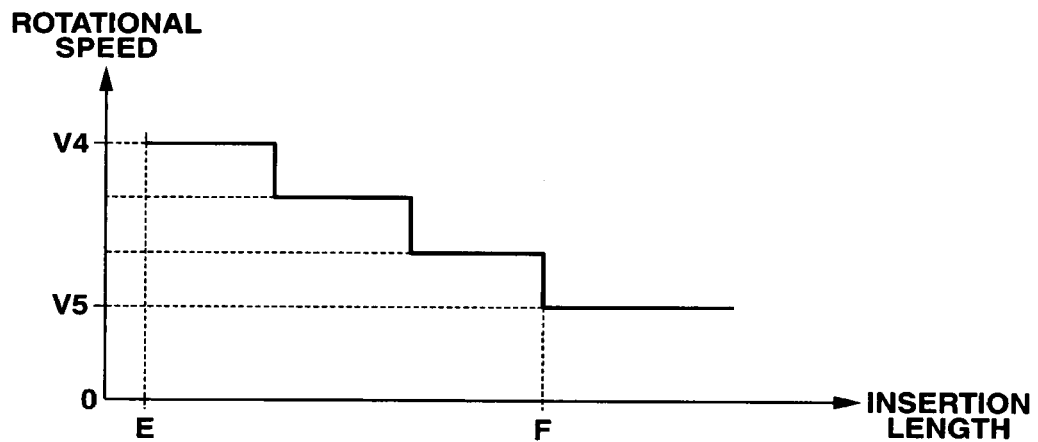
FIG. 13 is a view describing a relationship between changes in insertion lengths of the endoscope insertion portion having the spiral portion set to predetermined lengths and rotational speeds stepwisely decelerated with the changes.

A rotational speed may be decelerated in a stepwise manner from V4 to V5 as shown in FIG. 13 in place of continuous deceleration of a rotational speed from V4 to V5 as shown FIG. 12. In this case, deceleration step is not limited to four times shown in FIG. 13, but deceleration may be performed more than four times or less than four times.

The present invention includes such embodiments comprising combinations of part of the respective embodiments described above. For example, in the first embodiment, means (function) of monitoring a load in the motor monitor circuit 61 of the second embodiment may be provided. This enables the motor control circuit 51 to control so as to stop rotation of the motor 17 if the motor monitor circuit 61 determines a motor drive signal of a load level exceeding a predetermined load level.

The present invention is not limited to the above described embodiments, and various changes and modifications can be made without departing from the spirit and scope of the present invention.

What is claimed is:

1. An endoscope apparatus comprising:
an image pickup unit for performing an image pickup;
an insertion portion including a tube provided with a hole portion into which the image pickup unit is inserted, the tube having flexibility;
a thrust generating portion for generating a thrust by rotation, having a coil shape member wound on an outer-peripheral surface of the tube;
a rotation device for rotating the thrust generating portion around a longitudinal axis of the tube;
a length calculating portion for calculating a contact length of the thrust generating portion inserted into a subject in contact with the subject in a direction of the longitudinal axis; and
a control portion for controlling a rotational speed of the thrust generating portion to be variable according to the contact length calculated by the length calculating portion, so that the rotational speed reduces as the contact length increases, wherein
the coil shape member is formed in a solid-wound coil shape by winding a wire having a circular cross section on an outer-peripheral surface of the tube in the direction of the longitudinal axis such that the adjacent windings are in contact with each other, and
the thrust generating portion formed by the coil shape member on an entire outer circumferential surface of the insertion portion in the direction of the longitudinal axis except the distal end portion and a connector which is provided at a proximal end of the insertion portion and to which the rotation device is detachably connected.

2. The endoscope apparatus according to claim 1, wherein the thrust generating portion is a spiral shape portion having uneven portions formed into a spiral shape.

3. The endoscope apparatus according to claim 2, wherein the spiral shape portion is integrally provided on an outer-peripheral surface of the tube which constitutes the insertion portion, to form an endoscope insertion portion.

4. The endoscope apparatus according to claim 2, wherein the spiral shape portion is configured so as to be rotatably formed on an outer-peripheral surface of the insertion portion and the rotation device rotates the spiral shape portion alone.

5. The endoscope apparatus according to claim 2, wherein the insertion portion is provided detachably and reattachably from/on the rotation device.

6. The endoscope apparatus according to claim 1, comprising a rotational speed information storage portion storing preset information of rotational speeds for setting the rotational speed according to the contact length.

7. The endoscope apparatus according to claim 3, further comprising a traveling-amount detection mechanism for calculating a traveling amount of the endoscope insertion portion in an insertion-axis direction in contact with an outer-peripheral surface of the endoscope insertion portion,
wherein the length calculating portion calculates the contact length based on information obtained from the traveling-amount detection mechanism.

8. The endoscope apparatus according to claim 3, further comprising a motor monitoring portion for monitoring a motor drive signal electrically driving a motor for rotatingly driving the thrust generating portion,
wherein the length calculating portion calculates the contact length, based on a motor drive signal when a motor monitoring circuit determines that the motor rotates within a predetermined load range.

9. The endoscope apparatus according to claim 1, wherein the control portion controls the rotation device so as to stop the rotation if a rotational load of the thrust generating portion rotated by the rotation device exceeds a predetermined value.

10. The endoscope apparatus according to claim 1, wherein the rotation device has a setting portion for manually setting rotational speeds.

11. The endoscope apparatus according to claim 3, wherein the rotation device has a display portion for displaying the contact length calculated by the length calculating portion.

12. The endoscope apparatus according to claim 1, wherein the rotation device has a display portion for displaying a rotational speed of the thrust generating portion.

13. The endoscope apparatus according to claim 1, wherein the control portion sets the rotational speed in accordance with information of outer diameters of the thrust generating portion.

14. The endoscope apparatus according to claim 1, further comprising an insertion guide portion, the insertion guide portion enables the insertion portion to be inserted in the subject.

15. The endoscope apparatus according to claim 1, wherein the rotation device detects a rotational amount of the thrust generating portion around the longitudinal axis of the tube, and the length calculating portion calculates the contact length based on the rotational amount.

16. The endoscope apparatus according to claim 1, wherein the image pickup unit is provided at a distal end portion of the insertion portion.

17. The endoscope apparatus according to claim 1, wherein a connector provided at a proximal end of the insertion portion is detachably connected to the rotation device and the rotation device rotates the thrust generating portion around the longitudinal axis by rotating the connector, and the rotation device further comprises:
a signal line inserted through the insertion portion and having one end connected to the image pickup unit and the other end connected to electric contacts of the connector, and a signal processing device for driving the image pickup unit via the signal line and performing signal processing with respect to a signal obtained by the image pickup by the image pickup unit.

18. The endoscope apparatus according to claim 1, wherein the rotation device comprises a retainer detachably connected with the connector and a bearing for rotatably supporting the retainer.

19. The endoscope apparatus according to claim 18, wherein the rotation device further comprising a sensor for detecting a rotational angle around a longitudinal axis of the retainer detachably connected with the connector.

20. The endoscope apparatus according to claim 19, further comprising:
a signal processing device for driving the image pickup unit and performing signal processing with respect to a signal obtained by the image pickup by the image pickup unit,
wherein the sensor outputs a signal of the rotational angle to the signal processing device and the signal processing device performs processing for generating an image picked up by the image pickup unit in synchronism with the signal of the rotational angle.

21. The endoscope apparatus according to claim 1, further comprising a hollow protective tube provided outside of the subject and through which the insertion portion is inserted for retaining the insertion portion.

22. The endoscope apparatus according to claim 18, wherein the retainer has electric contact receivers detachably connected with electric contacts provided at the connector, and the electric contact receivers are electrically connected with a signal processing device for performing signal processing with respect to the image pickup unit via a slip ring which has rotor side electric contacts and stator-side electric contacts in contact with the rotor-side electric contacts and provided at the retainer.

23. The endoscope apparatus according to claim 18, wherein the rotation device comprises a first gear provided at the retainer and rotatable around a longitudinal axis of the retainer and a motor having a second gear engaged with the first gear on a rotating shaft.

24. The endoscope apparatus according to claim 1, wherein the thrust generating portion has two-layer structure in which the wire is further wound on an outer circumferential surface of the wire wound in a solid-wound coil shape.

25. The endoscope apparatus according to claim 1, wherein the outer circumferential surface of the insertion portion except the distal end portion and the connector which is provided at the proximal end of the insertion portion and detachably connected with the rotation device is formed by only a wire wound in a solid-wound coil shape.

* * * * *